(12) United States Patent
Schaible et al.

(10) Patent No.: US 6,596,219 B2
(45) Date of Patent: Jul. 22, 2003

(54) INFLATABLE MEMBER FORMED OF LIQUID CRYSTAL POLYMERIC MATERIAL BLEND

(75) Inventors: Stephen G. Schaible, Anaheim, CA (US); Debashis Dutta, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 95 days.

(21) Appl. No.: 09/970,817

(22) Filed: Oct. 3, 2001

(65) Prior Publication Data

US 2002/0081404 A1 Jun. 27, 2002

Related U.S. Application Data

(63) Continuation of application No. 09/394,235, filed on Sep. 13, 1999, now Pat. No. 6,325,780.

(51) Int. Cl.[7] .............................................. B29D 23/00
(52) U.S. Cl. ...................................... 264/515; 264/573
(58) Field of Search .................................. 264/515, 573

(56) References Cited

U.S. PATENT DOCUMENTS

| | | | |
|---|---|---|---|
| 4,963,313 A | 10/1990 | Noddin et al. ............... 264/573 |
| 4,966,807 A | 10/1990 | Harvey et al. ............... 428/220 |
| 5,078,700 A | 1/1992 | Lambert et al. ............. 604/264 |
| 5,156,785 A | * 10/1992 | Zdrahala ...................... 264/108 |
| 5,248,305 A | 9/1993 | Zdrahala ...................... 604/280 |
| 5,270,086 A | 12/1993 | Hamlin ........................ 428/35.2 |
| 5,306,246 A | * 4/1994 | Sahatjian et al. ......... 604/96.01 |
| 5,328,472 A | 7/1994 | Steinke et al. ............... 604/102 |
| 5,410,797 A | 5/1995 | Steinke et al. ................. 29/435 |
| 5,554,139 A | 9/1996 | Okajima ...................... 604/282 |
| 5,647,848 A | 7/1997 | Jørgensen ...................... 604/96 |
| 6,053,214 A | 4/2000 | Sjoberg et al. .............. 138/134 |
| 6,124,007 A | 9/2000 | Wang et al. ................. 428/35.2 |
| 6,165,158 A | 12/2000 | Dutta .......................... 604/265 |
| 6,242,063 B1 | 6/2001 | Ferrera et al. .............. 428/35.2 |
| 6,284,333 B1 | 9/2001 | Wang et al. ................. 428/35.5 |

FOREIGN PATENT DOCUMENTS

WO            99/12586        3/1999

\* cited by examiner

Primary Examiner—Suzanne E. McDowell
(74) Attorney, Agent, or Firm—Fulwider Patton Lee & Utecht, LLP

(57) ABSTRACT

A catheter having an inflatable member formed of a liquid crystal polymeric material. The inflatable member is formed from a blend of a minor amount, preferably less than 10%, of liquid crystal polymer with a major amount of a non-liquid crystal polymer having LCP fibers that are highly oriented in the machine direction. The aspect ratio of the liquid crystal polymeric material fibers is greater than 10, so that the polymer blend has mechanical characteristics similar to a fiber-reinforced composite with improved strength and optimal compliance.

7 Claims, 1 Drawing Sheet

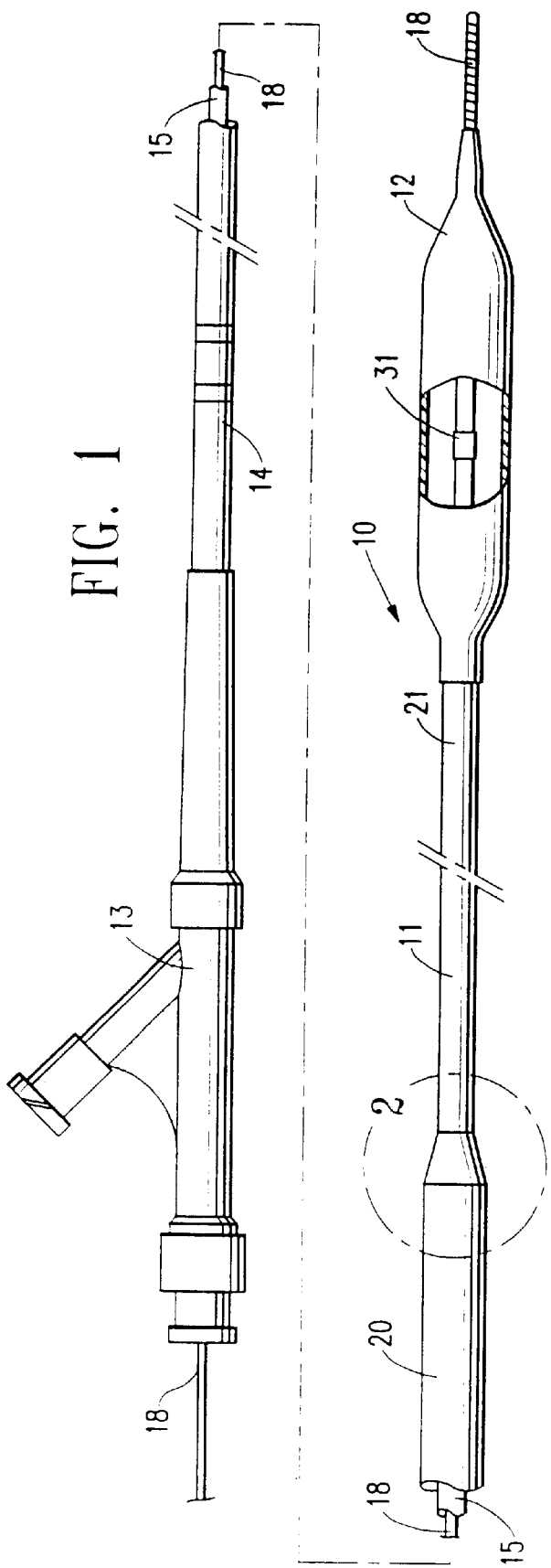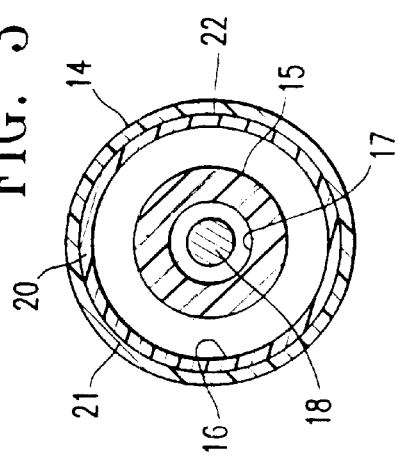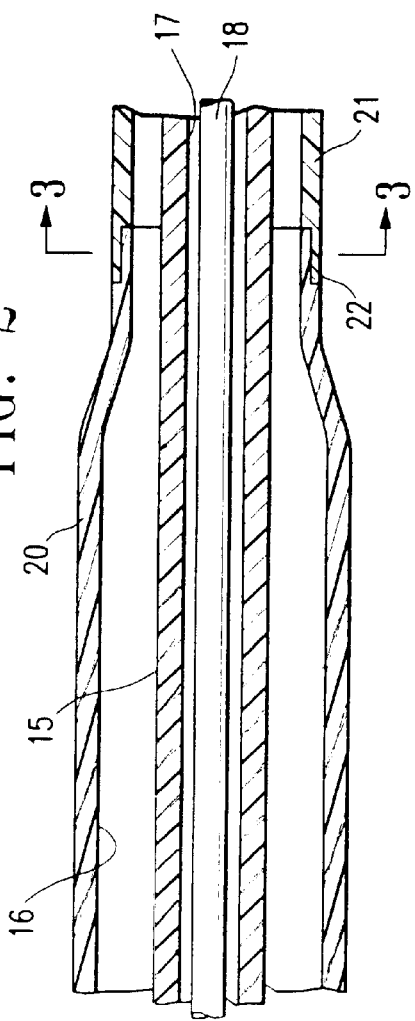

INFLATABLE MEMBER FORMED OF LIQUID CRYSTAL POLYMERIC MATERIAL BLEND

This application is a continuation of U.S. patent application Ser. No. 09/394,235, filed Sep. 13, 1999, now U.S. Pat. No. 6,325,780.

BACKGROUND OF THE INVENTION

This invention relates to the field of intravascular catheters, and more particularly to an inflatable member formed in part of liquid crystal polymeric material.

Balloon catheters generally comprise a catheter shaft with a inflatable member on the distal end of the shaft, and are used in a number of procedures, such as percutaneous transluminal coronary angioplasty (PTCA). In PTCA the balloon catheter is used to restore free flow in a clogged coronary vessel. The catheter is maneuvered through the patient's tortuous anatomy and into the patient's coronary anatomy until the inflatable member is properly positioned across the stenosis to be dilated. Once properly positioned, the inflatable member is inflated with liquid one or more times to a predetermined size at relatively high pressures (e.g. greater than 4 atm) to reopen the coronary passageway.

The material used to make the catheter inflatable member must have sufficient strength to contain the inflation fluid without bursting. In addition, the degree of compliance must be tailored so that the inflatable member expands during use, but does not overexpand and damage the body lumen. During extrusion and subsequent processing of polymeric inflatable member tubing, the longitudinal and radial orientation of the polymeric molecules can be tailored to increase the longitudinal and radial strength of the inflatable member produced therefrom. Because the force required to blow a inflatable member from tubing destroys some of the longitudinal orientation produced during extrusion, the extrusion process, and particularly the draw down ratio, is designed around optimizing the molecular orientation that is ultimately produced in the finished inflatable member. The strength of a inflatable member is typically expressed in terms of hoop strength and burst pressure.

Inflatable members formed from thermoplastics such as PET blended with liquid crystal polymers to improve the compliance of the inflatable member have been suggested (U.S. Pat. No. 5,306,246 (Sahatjian et al.)). However, Sahatjian et al. fails to address the problem of lower burst pressures of inflatable members produced from blends of a minor amount of liquid crystal polymer with a major amount of a non-liquid crystal polymer, relative to inflatable members produced from only thermoplastics such as PET.

Therefore, what has been needed is a catheter with an inflatable member having improved strength characteristics. The present invention satisfies these and other needs.

SUMMARY OF THE INVENTION

The invention is directed to a catheter which has an inflatable member formed of a polymeric blend comprising a minor amount of a liquid crystal polymeric material and a major amount of a non-liquid crystal polymeric material. There are many suitable liquid crystal polymeric materials that may be used, and a presently preferred example is VECTRA sold by Hoechst-Celanese. The non-liquid crystal polymeric material used in the LCP blend may be any extrudable thermoplastic polymer, and presently preferred examples are nylon 12 available from EMS, and PEBAX available from Atochem.

The LCP acts as reinforcement in the polymer matrix, similar to fiber reinforced composites, but at significantly lower dimensional scale and ease of processing. One presently preferred embodiment of the invention is a dilatation catheter which has an elongated catheter shaft and an inflatable dilatation member on a distal portion of the catheter. Conventional catheter design may be used, including over the wire, fixed wire and rapid exchange designs, having a single shaft with dual lumens or a multimembered shaft with inner and outer tubular members.

Liquid crystal polymers exhibit crystalline behavior in the liquid phase. The orientation of the molecules in the liquid state can be maintained in the solid state due to the long relaxation times of these molecules. The molecular orientation improves the strength of a polymeric component in the direction of orientation. The extent of molecular orientation can be expressed in terms of the Herman's orientation parameter (S) with a scale of from 0 (no orientation) to 1 (very highly oriented), which is a factor of the draw-down ratio (i.e. the ratio of the diameter of the die to the diameter of the finished extrudate) used during extrusion and viscosity. Liquid crystal polymers can be made to solidify after extrusion with an even greater degree of molecular orientation than ordinary polymers, and thus can be used to form ultra high strength articles. However, the high molecular orientation may result in disadvantageous characteristics in an inflatable member, such as little ability to withstand loads applied transverse to the orientation direction, increased stiffness, and poor bonding between layers. These disadvantages are avoided by the polymer blend of the invention. In the polymer blend of the invention, the Herman's orientation parameter is about 0.5 or less. Thus, the inflatable member of the invention formed from a minor amount of liquid crystal polymeric material existing as elongated liquid crystal polymeric fibers having an aspect ratio of about 10 to about 100, and preferably about 50 to about 100 has improved strength characteristics.

The inflatable member is formed from a blend comprising a minor amount, preferably less than about 20 to about 10 percent by weight of the blend, of liquid crystal polymeric material, with a major amount, preferably about 80 to about 90 percent by weight of the blend, of a non-liquid crystal polymeric material (hereafter, the LCP polymeric blend). By blending the liquid crystal polymeric material with another thermoplastic material the transverse strength of the inflatable member produced therefrom is increased. Additionally, it has been found that an inflatable member having LCP fibers that are highly oriented in the machine direction has improved mechanical characteristics. Specifically, if the aspect ratio of the liquid crystal polymer fibers is greater than 100, the LCP polymeric blend has mechanical characteristics similar to a continuous long-fiber-reinforced composite. As a result, the main load on the inflatable member is taken by the fibers (iso-strain process), as opposed to short fiber or dispersed phase composites where the load is shared by the filler and the matrix (iso-stress). Therefore, the LCP polymeric blend having a high aspect ratio can be used to produce thin walled inflatable members with improved burst pressures. Additionally, the risk of inflatable member overexpansion during use is reduced, because the high aspect ratio results in an advantageous reduction in inflatable member compliance.

An inflatable member formed from the LCP polymeric blend of the invention has improved strength and optimal compliance due to the high aspect ratio produced during extrusion. These and other advantages of the invention will become more apparent from the following detailed description of the invention and the accompanying exemplary drawings.

BRIEF DESCRIPTION OF THE DRAWINGS

FIG. 1 is an elevational view partially in section of a inflatable member catheter which embodies features of the invention.

FIG. 2 is a longitudinal cross-sectional view of the shaft of the catheter shown in FIG. 1, in circle 2.

FIG. 3 is a transverse cross-sectional view of the shaft shown in FIG. 2, taken along lines 3—3.

DETAILED DESCRIPTION OF THE INVENTION

As shown in FIG. 1, the catheter 10 of the invention generally includes an elongated catheter shaft 11 with an inflatable member 12 on a distal portion of the catheter shaft which has an interior in fluid communication with a lumen within the shaft, and an adapter 13 mounted on the proximal end of the catheter shaft.

The catheter shaft 11 has an outer tubular member 14 and an inner tubular member 15 disposed within the outer tubular member 14 and defining with the outer tubular member 14 an annular lumen 16 which is in fluid communication with the interior of the inflatable member 12. The inner tubular member 15 has an inner lumen 17 extending therein which is configured to slidably receive a guidewire 18 suitable for advancement through a patient's coronary arteries. The distal end of the inflatable member 12 is sealingly secured to the distal end of the inner tubular member 15 and the proximal end of the inflatable member 12 is secured to the distal end of the outer tubular member 16.

In the embodiment illustrated in FIG. 1, the outer tubular member 16 has a relatively stiff proximal shaft section 20 tapering to a smaller diameter and more flexible distal shaft section 21. The distal end of the proximal shaft section 20 is secured to the distal end of the distal shaft section 21 at lap joint 22 formed by suitable means such as heat or laser fusion or commercially available cyanoacrylate adhesive. However, a variety of suitable configurations may be used to connect the distal shaft section 21 to the proximal shaft section 20. The inner tubular member 15 extends the length of the catheter and may be formed of suitable materials, including but not limited to polyethylene, HYTREL, or the like.

Inflatable member 12 is formed from a blend of a minor amount of a liquid crystal polymeric material and a major amount of an non-LCP polymeric material (LCP polymeric blend). The LCP polymeric blend is extruded as tubing with high aspect ratio LCP fibers, which is then processed into an inflatable member 12 using conventional procedures. The melt processed, e.g. extruded, LCP polymeric blend has a high aspect ratio of about 10 to about 100, and preferably greater than 50, and most preferably greater than about 80. In the extrusion process, a high draw down ratio and a viscosity ratio close to unity is used to produce the high molecular orientation. The draw down ratio, as measured by the outer diameter of the extrusion die divided by the outer diameter of the extruded tubing, is not less than about 2, preferably not less than about 3, and is typically about 3 to about 10. The viscosity ratio is not less than about 1.1, and is typically about 1.1 to about 3.0. Because the inflatable member is produced from extruded tubing having a high aspect ratio, the load during pressurization of the inflatable member will be absorbed by the high strength LCP fibers. Consequently, the inflatable members of the invention have high hoop strength. The hoop strength is typically about 1200 atm to about 2500 atm, and preferably about 2000 atm. The burst pressure is about 14 atm to about 27 atm, and preferably about 23 atm, and the tensile strength is about 340 atm to about 1000 atm.

In a presently preferred embodiment, the inflatable member is formed by blow molding the extruded tube at 90° C. to 200° C., and 50 psi to 400 psi, depending on the thermoplastic material used. The extrusion process results in uniaxially oriented LCP fibers, and the blowing process imparts some radial orientation to the LCP fibers. Alternatively, a rotating die and/or mandrel extrusion can be used to produce an extrudate having fibers with longitudinal and radial orientation. The strength of the inflatable member is related to the longitudinal and radial orientation of the LCP fibers, and the extent of orientation should be tailored to ensure that the inflatable members produced will not have radial failure during use.

High strength inflatable members of the invention provide increased protection against the risk of bursting during pressurization, and can be used to produce strong, thin walled inflatable members. In an expanded state, the inflatable member outer diameter is generally about 0.1 cm to about 6 cm, and the length is about 10 mm to about 50 mm, and preferably about 20 mm.

A variety of suitable thermoplastic polymers may be used for the non-liquid crystal polymeric matrix in the LCP polymeric blend. The overall softness of the inflatable member can be improved by using soft thermoplastic elastomers or polyolefins. Alternatively, stiffer engineering polymers may be used as the matrix polymer. Presently preferred matrix polymers are polyether block amides such as PEBAX, and polyamides such as nylon 12. Suitable thermoplastic polymers include, but are not limited to, PET, PEEK, PEN, Nylon, HYTREL, VESTAMID, PPS, and polyethylene.

The liquid crystal polymeric material is a separate phase from the non liquid crystal polymeric material of the blend. Suitable liquid crystal polymeric materials are copolyesters, such as those sold under the trade name VECTRA, and polyesteramides such as XYDAR. In a presently preferred embodiment the invention, the liquid crystal polymeric material and matrix polymeric material are temperature-melt (T-melt) compatible, so that the polymers melt in the same temperature range. The T-melt compatibility is desirable because it avoids the polymer degradation that may otherwise result during extrusion.

In another embodiment, the blend may contain a small fraction of a compatibilizer to improve the adhesion between the LCP and the thermoplastic material, including ionomers such as metal neutralized sulfonated polystyrene, or polypropylene with maleic anhydride.

The length of the dilatation catheter 10 may be about 120 to about 150 cm in length, and typically is about 135 cm in length. The outer tubular member 14 has an OD of about 0.03 to about 0.05 inch (0.76–1.27 mm) and an ID of about 0.025 to about 0.035 inch (0.635–0.899 mm). The outer tubular member 14 may taper in its distal portion to a smaller OD of about 0.04 to about 0.02 inch (1.02–10.55 mm) and a smaller ID of about 0.03 to about 0.015 inch (0.762–0.381). The smaller diameter portion between the taper and the proximal extremity of the inflatable member 12 may be about 5 to about 25 cm in length.

The inner tubular member 15 has an OD ranging from about 0.018 to about 0.026 inch (0.457–0.66 mm), and the ID of the inner tubular member will usually be determined by the diameter of the guidewire 18 which is to be used with the catheter, which may range from about 0.008 to about 0.02 inch (0.203–0.51 mm). The inner diameter of the inner lumen should be about 0.002 to about 0.005 inch (0.051–0.127 mm) larger than the OD of the guidewire 18 to be used. Usually there will be a family of catheters for each size of guidewire with a variety of maximum inflated inflatable member sizes, e.g., 0.5 to about 4 mm in diameter and with various working lengths ranging from about 1 to about 10 cm.

To the extent not previously described herein, the various catheter components may be formed of conventional materials. For example, radiopaque marker 31 may be a gold band and the adapter body may be formed of polycarbonate polymers.

While the present invention has been described in terms of certain preferred embodiments, those skilled in the art will recognize that modifications and improvements may be made to the invention without departing from the scope thereof. For example, while the catheter illustrated has an outer tubular member with proximal and distal sections, and an inner tubular member, a variety of suitable shaft designs may be used including a dual lumen shaft.

What is claimed is:

1. A method of making an inflatable member for a catheter, comprising:
    a) extruding a blend comprising a major amount of non-liquid crystal polymeric material and a minor amount of liquid crystal polymeric material at a draw down ratio of not less than about 2 to form an extruded tube having liquid crystal polymeric elongated fibers, the fibers having an aspect ratio of not less than about 10; and
    b) processing the extruded tube to form the inflatable member.

2. The method of claim 1 wherein the draw down ratio is about 3 to about 10.

3. The method of claim 1 wherein at least one of a extruder mandrel and extruder die are rotated during extrusion to radially orient the liquid crystal polymeric fibers.

4. The method of claim 1 wherein processing the extruded tube includes expanding the extruded tube to form the inflatable member.

5. The method of claim 1 wherein (b) comprises blow molding the extruded tube in a balloon mold.

6. The method of claim 1 wherein the blend is extruded at a draw down ratio of not less than about 3, to form the extruded tube having liquid crystal polymeric elongated fibers, the aspect ratio of the fibers being greater than about 50.

7. A method of making an inflatable member for a catheter, comprising:
    a) extruding a blend comprising a major amount of non-liquid crystal polymeric material and a minor amount of liquid crystal polymeric material to form an extruded tube having liquid crystal polymeric elongated fibers, the fibers having an aspect ratio of greater than about 50; and
    b) processing the extruded tube to form the inflatable member.

* * * * *

UNITED STATES PATENT AND TRADEMARK OFFICE
CERTIFICATE OF CORRECTION

PATENT NO.      : 6,596,219 B2
DATED           : June 10, 2003
INVENTOR(S)     : Stephen G. Schaible et al.

It is certified that error appears in the above-identified patent and that said Letters Patent is hereby corrected as shown below:

Title page,
Item [63], Related U.S. Application Data, change "Continuation" to read
-- Divisional --.

Column 1,
Line 5, change "continuation", to read -- divisional --.

Signed and Sealed this

Twenty-third Day of December, 2003

JAMES E. ROGAN
*Director of the United States Patent and Trademark Office*